United States Patent
Aker

[11] Patent Number: 6,152,738
[45] Date of Patent: Nov. 28, 2000

[54] METHOD AND APPARATUS FOR A PROSTHETIC LIGAMENT

[76] Inventor: Frank Aker, Apt. 2DE, 10346 Conser, Overland Park, Kans. 66212

[21] Appl. No.: 09/401,464

[22] Filed: Sep. 22, 1999

[51] Int. Cl.[7] .................................................... A61C 8/00
[52] U.S. Cl. ............................ 433/173; 433/174; 433/177
[58] Field of Search ................................ 433/173, 177, 433/169, 174, 201.1

[56] References Cited

U.S. PATENT DOCUMENTS

| | | | |
|---|---|---|---|
| 4,731,085 | 3/1988 | Koch | 433/177 X |
| 5,453,007 | 9/1995 | Wagher | 433/177 |
| 5,954,505 | 9/1999 | Ford | 433/177 |

Primary Examiner—Nicholas D. Lucchesi
Attorney, Agent, or Firm—Michael I. Kroll

[57] ABSTRACT

The present invention 10 discloses a method and apparatus for replicating the force absorption capabilities of natural teeth 28. Provided therein is a periodontal implant 10 which functions as a cup-like housing 10 for receiving an additional implant 32 or avulsed teeth. The implant 10 is externally threaded 12 for connection to the jaw bone 24 and internally threaded 14 for receiving the additional implant 32. The periodontal ligament 10 is fabricated from materials having a low modulus of elasticity, without causing deformation of the periodontal ligament implant. Materials of construction may include natural, synthetic, biological or genetically engineered materials.

20 Claims, 6 Drawing Sheets

METHOD AND APPARATUS FOR A PROSTHETIC LIGAMENT

BACKGROUND OF THE INVENTION

1. Field of the Invention

The present invention relates generally to prosthetic teeth and more specifically to a method and apparatus for imitating the force absorption capabilities of natural teeth by providing a periodontal ligament implant which will function as a housing for implants or avulsed teeth. Said periodontal implant is comprised of means for attaching said implant to a host bone and means for preventing osseointegration of associated implants by prevent the associated implant or avulsed teeth from coming into contact with the bone. This may presently be accomplished by, but not limited to, bonding a periodontal ligament implant to the alveolus using such material well known in the art such as hydroxyapitite.

The periodontal ligament is fabricated from materials having a low modulus of elasticity, without causing deformation of the periodontal ligament implant. Therein, providing means for permitting the implant to function as a normal tooth under masticatory loads.

As a consequence, the prosthetic implant permits the adjacent normal teeth to function naturally by not inhibiting the oral cavity's occlusal forces which are exhibited in micro movements and hydrostatic cushioning.

2. Description of the Prior Art

There are numerous methods and devices for implanting prosthetic teeth. The most popular involving some type of post implanted into the jawbone whereupon is mounted some type of crown. While these posts have evolved from cylindrical screws which were threaded into the jawbone after drilling appropriately sized holes. To blade implants which were basically rectangular implants which were frictionally fitted into longitudinal troughs. To the presently popular titanium posts which permitted osseointegration, the bone bonds to the titanium post forming a durable anchorage for the attachment of crowns. While all of these methods enjoy limited success, they all suffer from a common flaw in that they are in contact with the bone.

A natural tooth has a periodontal ligament or membrane which is highly specialized tissue and tissue-like fibers that form in the alveolus between the alveolar bone proper and cementum. This cellular connective tissue between the alveolar bone proper and cementum is responsible for dissipating the forces generated during mastication on the alveolar bone. The present system concentrates these force by having rigid member affixed to the bone which can lead to bone deteriorate or fracture.

Therefore, it is felt that a need exist for providing a periodontal ligament implant which will function as a receptor for associated implant. It is further desirable to provide a periodontal implant which can be used as a receptor for avulsed teeth to prevent resorption and fracture.

SUMMARY OF THE PRESENT INVENTION

The present invention discloses a method and apparatus for a device made from materials with a low modulus of elasticity for replicating the force absorption capabilities of natural teeth. Provided therein is a periodontal implant which functions as a cup-like housing for receiving an additional implant or avulsed teeth. The implant is externally threaded for connection to the jaw bone and internally threaded for receiving the additional implant. The periodontal ligament is fabricated from materials having a low modulus of elasticity, without causing deformation of the periodontal ligament implant. Materials of construction may include natural, synthetic, biological or genetically engineered materials A primary object of the present invention is to provide a synthetic periodontal ligament.

Another object of the present invention is to provide a device having means for attaching an associated implant.

A yet further object of the present invention is to provide a device which will encompass and prevent an associated implant from osseointegration.

A still further object of the present invention is to provide a device having the force absorption capabilities of natural periodontal ligament.

Another object of the present invention is to provide a device having a low modulus of elasticity, without causing deformation of the device.

Additional objects of the present invention will appear as the description proceeds.

The present invention overcomes the shortcomings of the prior art devices by providing a method and apparatus for imitating the force absorption capabilities of natural teeth through a periodontal ligament implant which will function as a receptor for implants or avulsed teeth. Said periodontal implant has means for attaching the implant to a host bone and means for preventing osseointegration of associated implants.

The periodontal ligament is fabricated from materials having a low modulus of elasticity, without causing deformation of the periodontal ligament implant. Therein, providing means for permitting the implant to function as a normal tooth under masticatory loads. The prosthetic ligament may be made from natural, synthetic, biological, or genetically engineered material.

As a consequence, the prosthetic implant permits the adjacent normal teeth to function naturally by not inhibiting the oral cavity's occlusal forces which are exhibited in micro movements and hydrostatic cushioning.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become more fully appreciated as the same becomes better understood when considered in conjunction with the accompanying drawings, in which like reference characters designate the same or similar parts throughout the several views.

REFERENCE NUMERALS

Figure 1:
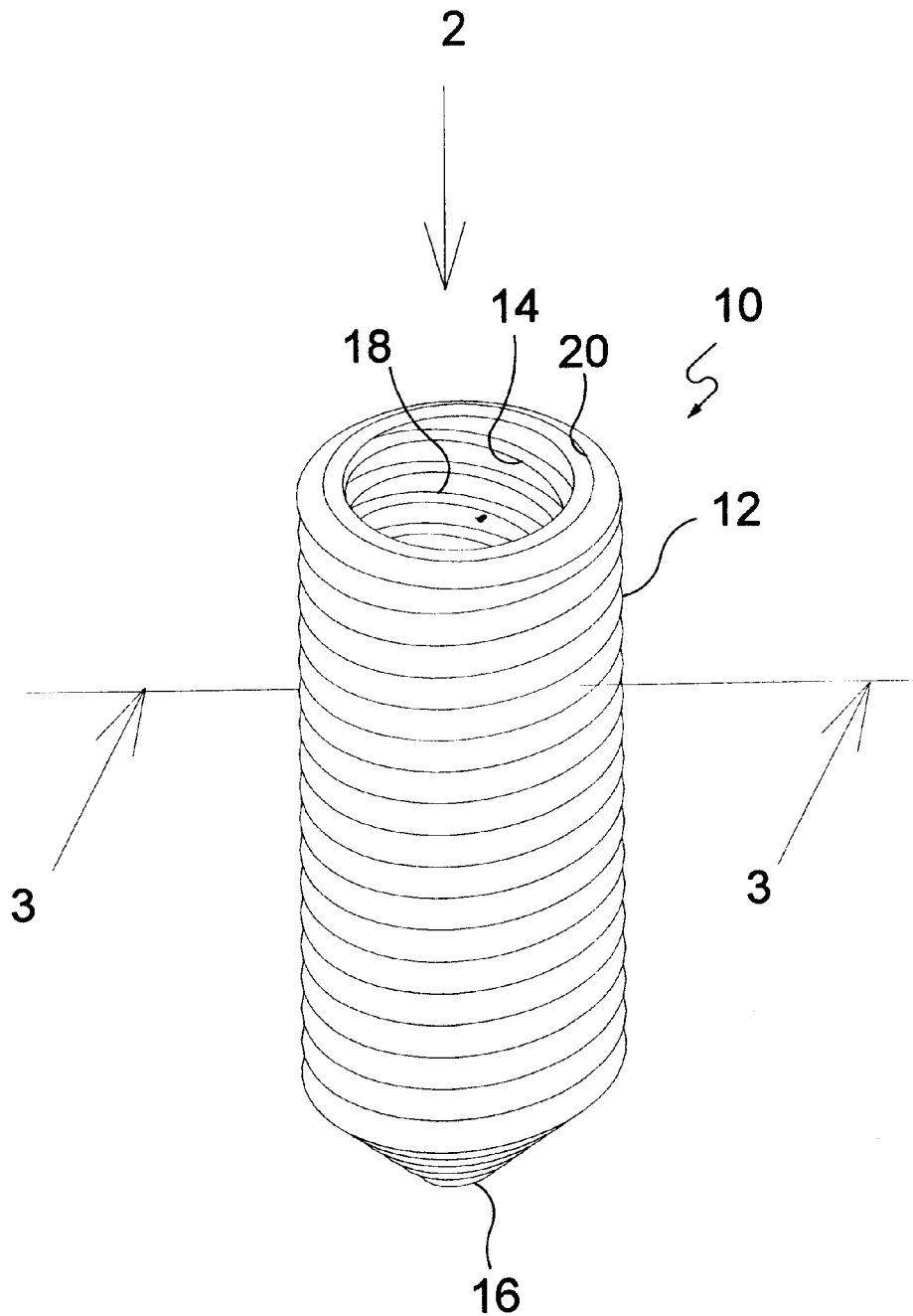
FIG. 1 is a perspective view of the present invention. Shown is a periodontal ligament implant which will function as a housing for implants or avulsed teeth.

With regard to reference numerals used, the following numbering is used throughout the drawings.
10 present invention
12 exterior threads
14 interior threads
16 lower end
18 opening
20 wall
22 base infrastructure
24 jaw bone
26 gums
28 teeth
30 missing tooth location
32 implant
34 implant threads
36 cavity

DESCRIPTION OF THE PREFERRED EMBODIMENT(S)

In order that the invention may be more fully understood, it will now be described, by way of example, with reference to the accompanying drawings in which FIGS. 1 through 7 illustrate the present invention being a method and apparatus of a prosthetic ligament.

Turning to FIG. 1, shown therein is a perspective view of the present invention 10. Shown is a periodontal ligament implant 10 which will function as a housing for implants or avulsed teeth. The housing 10 is a generally upright standing cup-like member being pointed on the lower end 16 having an opening 18 on the upper end. The periodontal implant 10 has exterior threaded means 12 for adhering to a bone socket. The threads 12 can have an amount of bonding material such as hydroxyapitite placed thereon. Interior threaded means 14 are also shown.

The periodontal ligament 10 is fabricated from materials having a low modulus of elasticity, without causing deformation of the periodontal ligament implant. Therein, providing means for permitting the implant to function as a normal tooth under masticatory loads.

Figure 2:
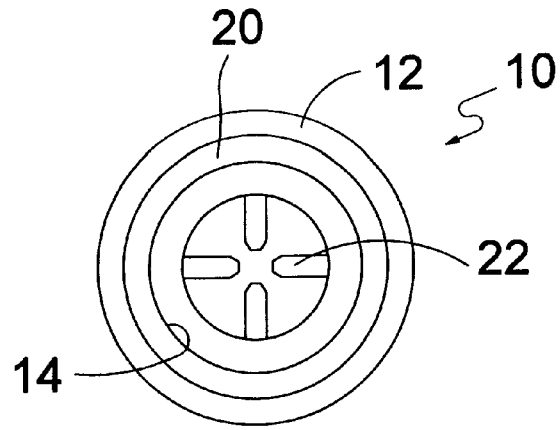
FIG. 2 is a top plan view of the present invention, taken from FIG. 1 as indicated. Shown is a periodontal ligament implant which will function as a housing for implants or avulsed teeth.

Turning to FIG. 2, shown therein is a top plan view of the present invention 10, taken from FIG. 1 as indicated. Shown is a periodontal ligament implant 10 which will function as a housing with wall 20 for implants or avulsed teeth. The periodontal implant has exterior threaded means 12 for adhering to a bone socket. The threads 12, 14 can have an amount of bonding material such as hydroxyapitite placed thereon.

The periodontal ligament 10 is fabricated from materials having a low modulus of elasticity, without causing deformation of the periodontal ligament implant 10. Therein, providing means for permitting the implant to function as a normal tooth under masticatory loads.

Also shown are interior threads 14 providing secure means for associated implants. In addition the periodontal implant 10 has a base infrastructure 22 providing means for inserting tools which will exert rotational torque in seating the implant 10 within the bone cavity.

Figure 3:
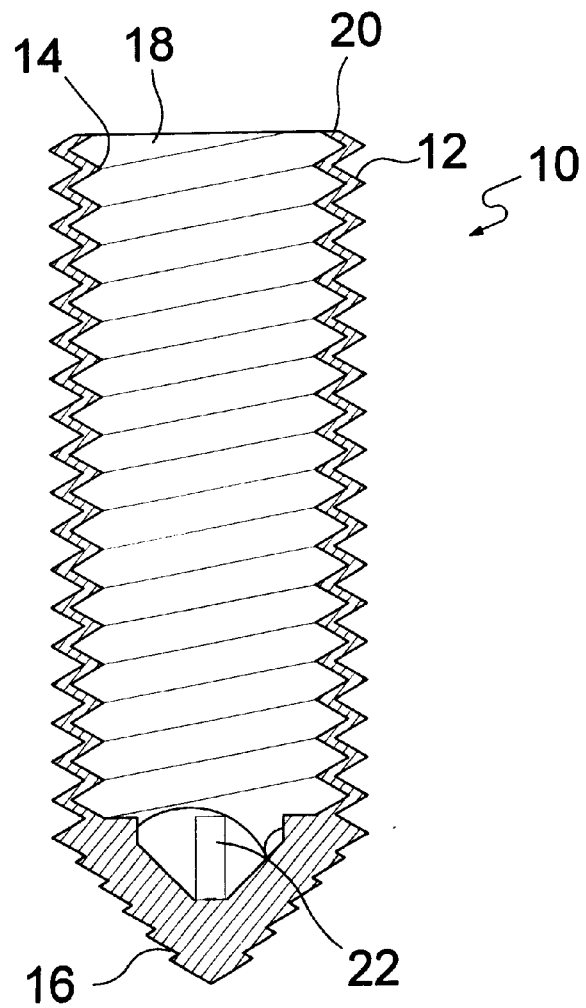
FIG. 3 is a cross section view of the present invention, taken from FIG. 1 as indicated. Shown is a periodontal ligament implant which will function as a housing for implants or avulsed teeth

Turning to FIG. 3, shown therein is a cross section view of the present invention 10, taken from FIG. 1 as indicated. Shown is a periodontal ligament implant 10 which will function as a housing with walls 20 for implants or avulsed teeth. The periodontal implant 10 has exterior threaded means 12 for adhering to a bone socket, The threads can have an amount of bonding material such as hydroxyapitite.

The periodontal ligament 10 is fabricated from materials having a low modulus of elasticity, without causing deformation of the periodontal ligament implant. Therein, providing means for permitting the implant to function as a normal tooth under masticatory loads.

Also shown are interior threads 14 providing securement means for associated implants. 1n addition the periodontal implant has a base infrastructure 22 providing means for inserting tools which will exert rotational torque in seating the implant within the bone cavity. Aperture 18 is also shown along with lower end or tip 16.

Figure 4:
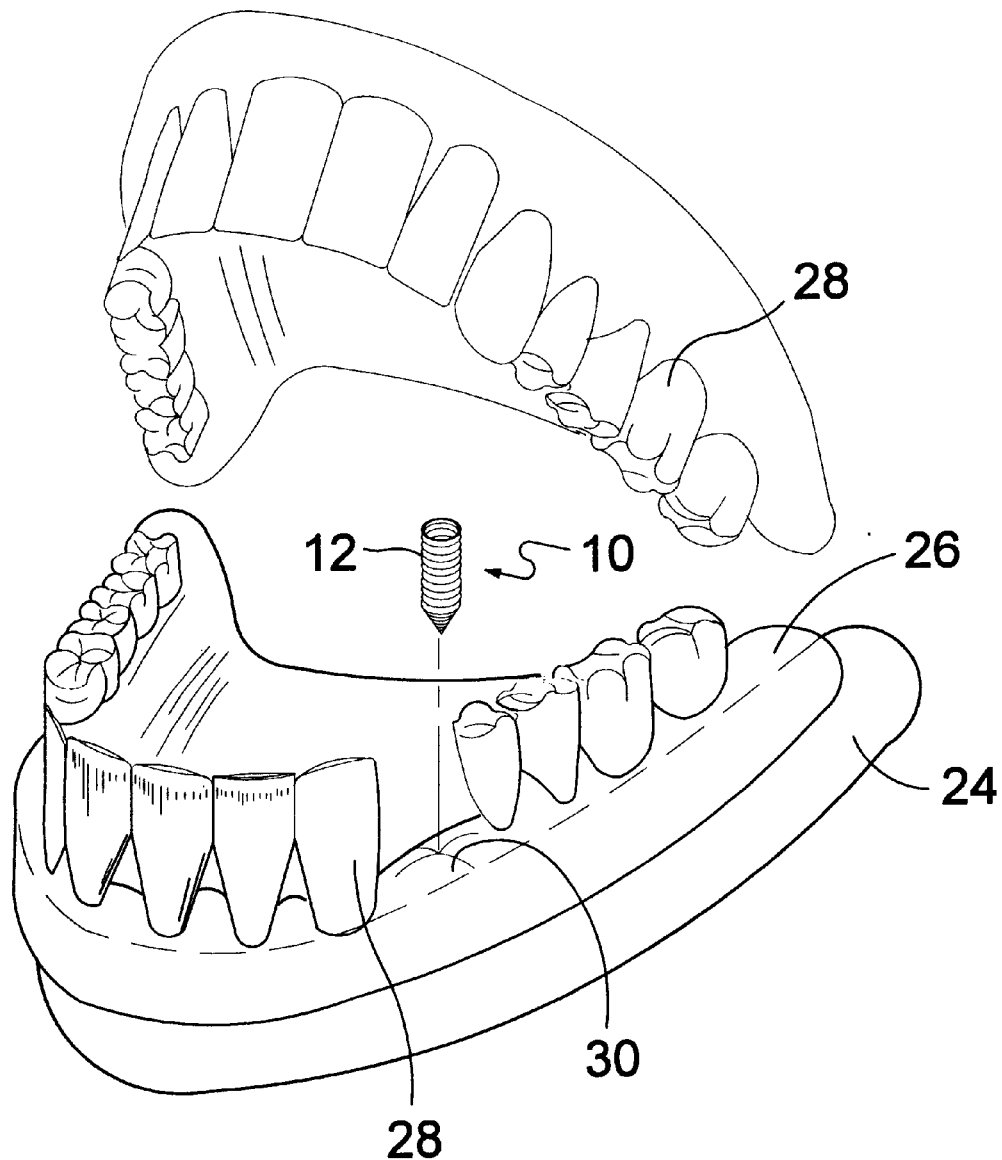
FIG. 4 is an illustrative vie of the present invention ready to be installed. Shown is the periodontal ligament implant which will function as a housing for additional implants or avulsed teeth.

Turning to FIG. 4, shown therein is an illustrative view of the present invention 10 ready to be installed into a location 30 where there is a missing tooth. Shown is the periodontal ligament implant 10 which will function as a housing for additional implants or avulsed teeth. The periodontal implant has exterior threaded means 12 for adhering to a bone socket.

Also shown are a human jaw bone 24 with gums 26 and associated teeth 28.

Figure 5:
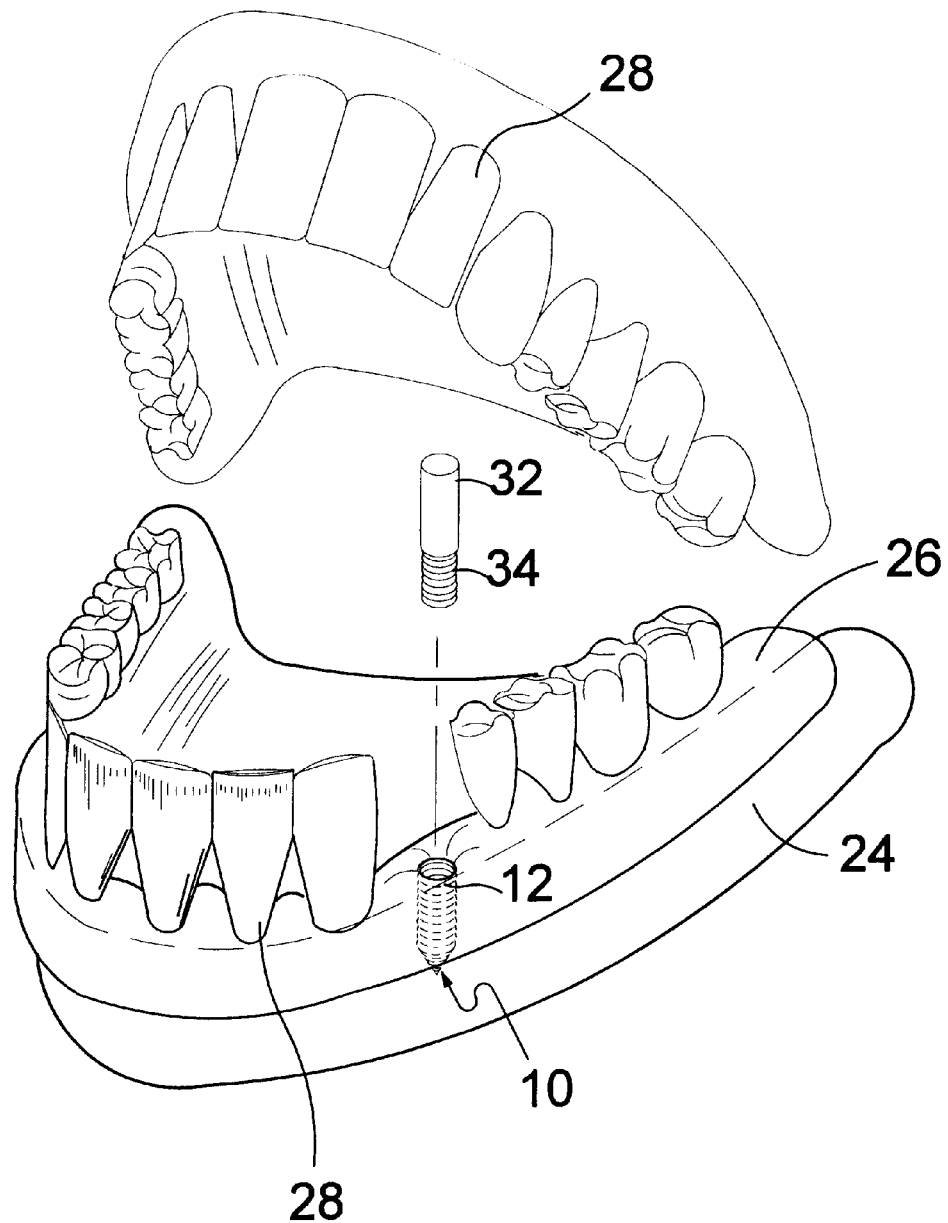
FIG. 5 is a continued illustrative view as shown in FIG. 4. Shown is the periodontal ligament implant positioned with the jawbone which will function as a housing for additional implants or avulsed teeth.

Turning to FIG. 5, shown therein is a continued illustrative view as shown in FIG. 4. Shown is the periodontal ligament implant 10 positioned within the jawbone 24 and gums 26 within which implant 10 will function as a housing for additional implants, e.g., 32, or avulsed teeth. The periodontal implant has exterior threaded means 12 for adhering to a bone socket. implant 32 has mating male threaded means 34 for communication with the interior female threaded means 14 of the present invention 10.

Figure 6:
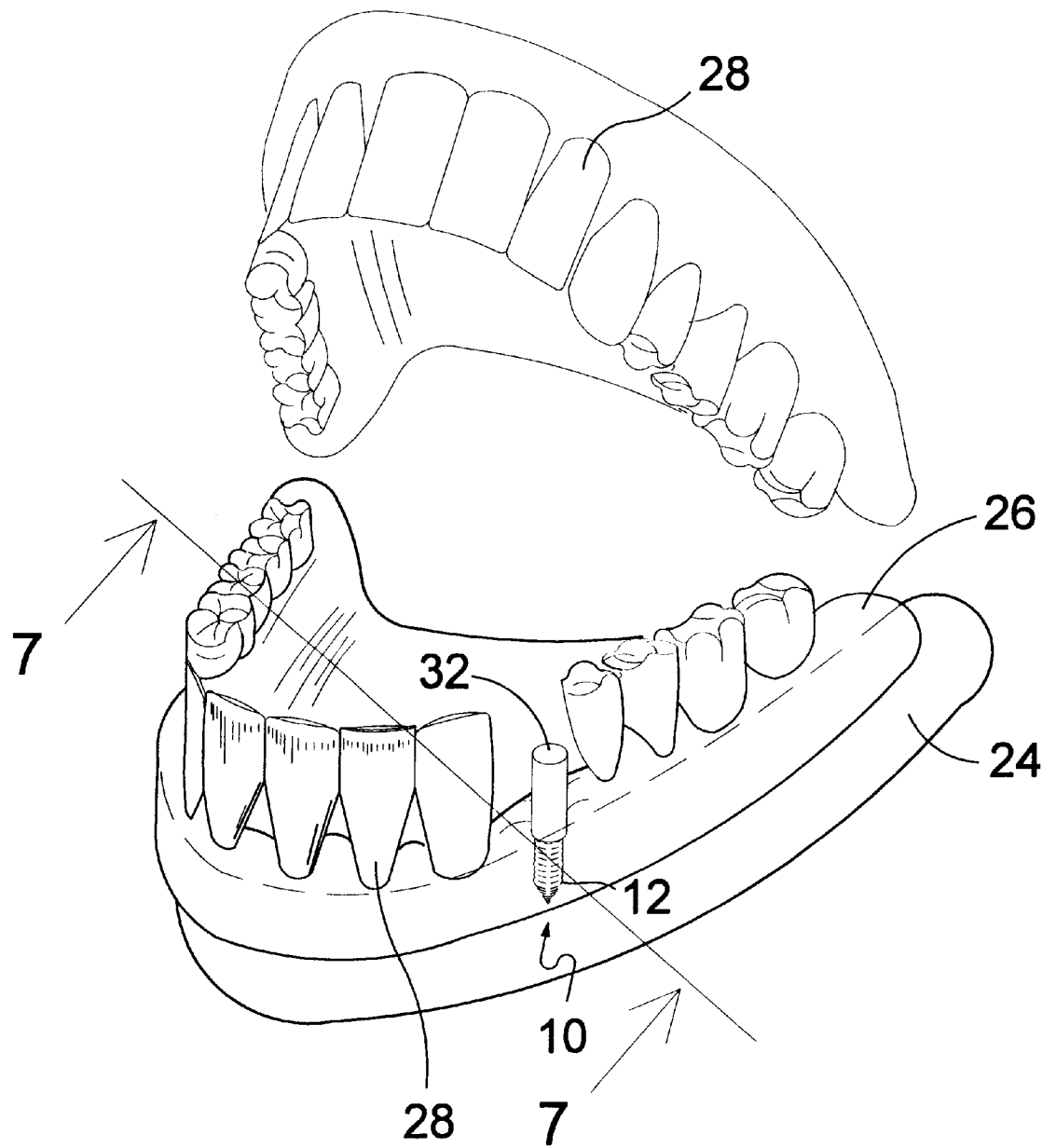
FIG. 6 is a continued illustrative view as shown in FIG. 5. Shown is the periodontal ligament implant positioned with the jawbone housing an additional implant.

Turning to FIG. 6, shown therein is a continued illustrative view as shown in FIG. 5. Shown is the periodontal ligament implant positioned within the jawbone 24 and gums 26 for housing an additional implant. The periodontal implant 10 has exterior threaded means 12 for adhering to a bone socket. The periodontal implant 10 has interior threaded means whereby the additional implant 22 can be affixed thereto.

The periodontal ligament 10 is fabricated from materials having a low modulus of elasticity, without causing deformation of the periodontal ligament implant. Therein, providing means for permitting the additional implant 32 to function in a normal fashion under masticatory loads. The prosthetic ligament 10 may be made from natural, synthetic, biological or genetically engineering material.

Figure 7:
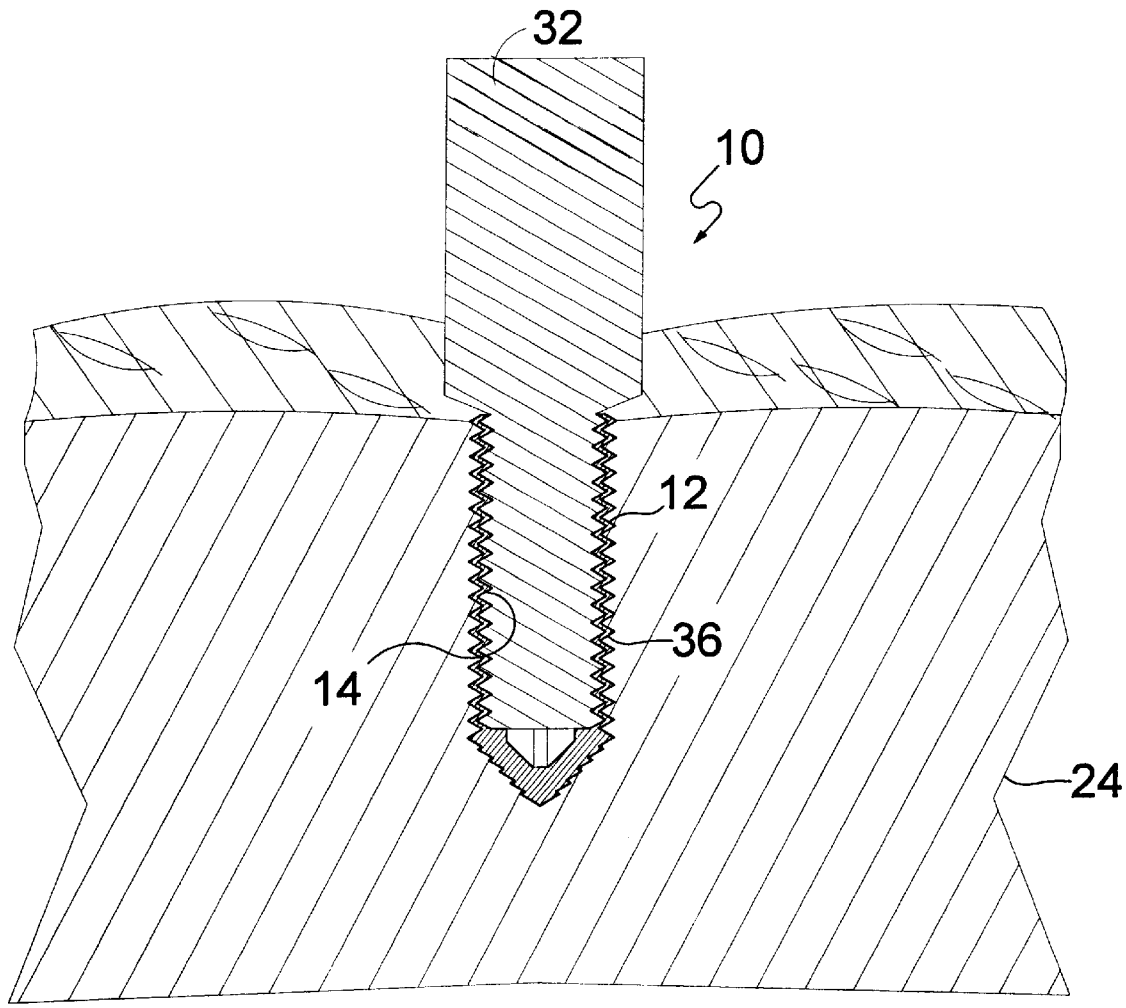
FIG. 7 is a cross sectional view of the present invention, taken from FIG. 6 as indicated. Shown is the phosthetic periodoutal implant unfixed within a cavity within the bone.

Turning to FIG. 7, shown therein is a cross sectional view of the present invention 10, taken from FIG. 6 as indicated. Shown is the prosthetic periodontal implant 10 affixed within a cavity 36 within the jaw bone 24. The exterior threads 12 of the periodontal implant 10 can have an amount of bonding material such as hydroxyapitite. The interior of the prosthetic periodontal ligament 10 has interior threads 14 whereby the additional implant 32 having threads 34 can be affixed thereto. The additional implant 32 being encompassed within the jaw bone 24 structure will function in a similar manner as natural teeth 28 having force absorption capability. Further the additional implant 32, lacking contact with the bone 24 will not become osseointegrated with the bone 24.

I claim:

1. An apparatus for a prosthetic tooth for attachment to a human jaw bone, comprising:
   a) a cup-like generally upright standing housing being hollow therein having an opening on a first end and being pointed on a second end, said second end being the lower end;
   b) said cup-like housing fabricated from materials having a low modulus of elasticity, whereby said housing functions as a normal tooth under masticatory loads;
   c) external fastening means positioned on said cup-like housing, said external fastening means for attachment to the jaw bone, whereby said cup-like housing is fastened to the jaw bone;
   d) internal fastening means positioned interior of said cup-like housing, whereby an implant can be fastened to said cup-like housing; and,
   e) an implant for being fastened to said internal fastening means of said cup-like housing.

2. The apparatus of claim 1, said external fastening means further comprising threaded means.

3. The apparatus of claim 1, said internal fastening means further comprising threaded means.

4. The apparatus of claim 1, said cup-like housing further comprising means for receiving dental tools, said dental tools for rotationally turning said housing whereby said housing is fastened to the jaw bone.

5. The apparatus of claim 4, said means for receiving dental tools further comprising multiple protrusions for receiving dental tools.

6. The apparatus of claim 5, wherein said multiple protrusions are mounted internal of said housing.

7. The apparatus of claim 5, wherein said multiple protrusions are mounted on the lower end of said housing.

8. The apparatus of claim 1, said implant further comprising mating fastening means on a first lower end for communication with said internal fastening means of said housing.

9. The apparatus of claim 8, said mating fastening means further comprising threaded means whereby said implant is fastened to said cup-like housing.

10. The apparatus of claim 8, said implant further comprising a natural tooth surface on a second upper end.

11. The apparatus of claim 8, said implant further comprising a post on a second upper end.

12. The apparatus of claim 1, wherein the apparatus of made of natural material.

13. The apparatus of claim 1, wherein the apparatus is made of synthetic material.

14. The apparatus of claim 1, wherein the apparatus is made of biologically engineered material.

15. The apparatus of claim 1, wherein the apparatus is made of genetically engineered material.

16. The apparatus of claim 1, further comprising bonding material means whereby said cup-like housing is bonded to the jaw bone.

17. A method for providing prosthetic teeth to a human jaw, comprising the steps of:
   a) providing a cavity in the jaw bone for placement therein of a prosthesis;
   b) providing a cup-like generally upright standing housing being hollow therein having an opening on a first end and being pointed on a second end, said second end being the lower end;
   c) fabricating said cup-like housing from materials having a low modulus of elasticity, whereby said housing functions as a normal tooth under masticatory loads;
   d) placing external fastening means on said cup-like housing, said external fastening means for attachment to the jaw bone, whereby said cup-like housing is fastened to the jaw bone;
   e) placing internal fastening means on the interior of said cup-like housing, whereby an implant can be fastened to said cup-like housing; and,
   f) providing an implant for being fastened to said internal fastening means of said cup-like housing.

18. The method of claim 17, further comprising the step of drilling said cavity in the jaw bone for placement therein of the prosthesis.

19. The method of claim 17, further comprising the step of placing external threads on said cup-like housing, said external threads for attachment to the jaw bone, whereby said cup-like housing is fastened to the jaw bone.

20. The method of claim 17, further comprising the step of providing a bonding material to said cup-like housing, whereby said cup-like housing is bonded to the jaw bone.

* * * * *